(12) United States Patent
Hassan et al.

(10) Patent No.: US 10,967,105 B2
(45) Date of Patent: Apr. 6, 2021

(54) MEDICAL DEVICES AND INSTRUMENTS WITH NON-COATED SUPERHYDROPHOBIC OR SUPEROLEOPHOBIC SURFACES

(71) Applicants: Tarek Hassan, Ann Arbor, MI (US); Tushar M. Ranchod, Berkeley, CA (US)

(72) Inventors: Tarek Hassan, Ann Arbor, MI (US); Tushar M. Ranchod, Berkeley, CA (US)

(*) Notice: Subject to any disclaimer, the term of this patent is extended or adjusted under 35 U.S.C. 154(b) by 701 days.

(21) Appl. No.: 14/452,681

(22) Filed: Aug. 6, 2014

(65) Prior Publication Data
US 2015/0044421 A1 Feb. 12, 2015

Related U.S. Application Data

(60) Provisional application No. 61/863,128, filed on Aug. 7, 2013.

(51) Int. Cl.
*A61L 31/14* (2006.01)
*A61L 27/50* (2006.01)
(Continued)

(52) U.S. Cl.
CPC .............. *A61L 31/14* (2013.01); *A61L 27/50* (2013.01); *B23K 15/0006* (2013.01);
(Continued)

(58) Field of Classification Search
CPC .... B32B 3/30; B32B 3/26; B32B 3/24; B32B 3/00; Y10T 428/24355–24771;
(Continued)

(56) References Cited

U.S. PATENT DOCUMENTS 8,043,359 B2  10/2011  Edin
8,707,999 B2   4/2014  Kim et al.
(Continued)

FOREIGN PATENT DOCUMENTS

WO    2006135755 A2   12/2006
WO    2009158336 A1   12/2009
(Continued)

OTHER PUBLICATIONS

Bhushan B., et al., "Micro-, Nano- and Hierarchical Structures for Superhydrophobicity, Self-Cleaning and Low Adhesion," Phil. Trans. R. Soc. A, 367:1631-1672, 2009.

*Primary Examiner* — Maria V Ewald
*Assistant Examiner* — Ethan A. Utt
(74) *Attorney, Agent, or Firm* — Law Offices of John G. Posa

(57) ABSTRACT

Device surfaces are rendered superhydrophobic and/or superoleophobic through microstructures and/or nanostructures that utilize the same base material(s) as the device itself without the need for coatings made from different materials or substances. A medical device includes a portion made from a base material having a surface adapted for contact with biological material, and wherein the surface is modified to become superhydrophobic, superoleophobic, or both, using only the base material, excluding non-material coatings. The surface may be modified using a subtractive process, an additive process, or a combination thereof. The product of the process may form part of an implantable device or a medical instrument, including a medical device or instrument associated with an intraocular procedure. The surface may be modified to include micrometer- or nanometer-sized pillars, posts, pits or cavitations; hierarchical structures having asperities; or posts/pillars with caps having dimensions greater than the diameters of the posts or pillars.

10 Claims, 5 Drawing Sheets

(51) Int. Cl.
    *B23K 26/00*    (2014.01)
    *B23K 15/08*    (2006.01)
    *B29C 59/14*    (2006.01)
    *B23K 26/352*    (2014.01)
    *B23K 15/00*    (2006.01)
    *B29C 59/16*    (2006.01)
    *C04B 41/91*    (2006.01)
    *B23K 103/04*    (2006.01)
    *B23K 103/08*    (2006.01)
    *B23K 103/00*    (2006.01)
    *B23K 103/18*    (2006.01)
    *B29L 31/00*    (2006.01)
    *C04B 111/00*    (2006.01)

(52) U.S. Cl.
    CPC .......... *B23K 15/08* (2013.01); *B23K 26/0006* (2013.01); *B23K 26/355* (2018.08); *B29C 59/14* (2013.01); *B29C 59/16* (2013.01); *C04B 41/91* (2013.01); *A61L 2400/18* (2013.01); *B23K 2103/05* (2018.08); *B23K 2103/08* (2018.08); *B23K 2103/26* (2018.08); *B23K 2103/50* (2018.08); *B29C 2791/009* (2013.01); *B29K 2995/0092* (2013.01); *B29K 2995/0093* (2013.01); *B29L 2031/753* (2013.01); *C04B 2111/00025* (2013.01); *Y10T 428/24* (2015.01); *Y10T 428/24355* (2015.01)

(58) Field of Classification Search
    CPC ..... Y10T 428/24174; Y10T 428/24182; Y10T 428/24479; Y10T 428/2457; Y10T 428/24587; A61F 9/00; A61F 9/007

USPC .................................. 428/156–173, 119, 120
See application file for complete search history.

(56)             References Cited

U.S. PATENT DOCUMENTS

| | | |
|---|---|---|
| 8,746,375 B2 | 6/2014 | Hendrik et al. |
| 2004/0208791 A1 * | 10/2004 | Extrand .................. B01L 9/527 |
| | | 428/156 |
| 2007/0005024 A1 | 1/2007 | Weber et al. |
| 2008/0154245 A1 | 6/2008 | Martin |
| 2009/0234274 A1 * | 9/2009 | Luloh .................. A61F 9/00763 |
| | | 604/22 |
| 2010/0028604 A1 | 2/2010 | Bhushan et al. |
| 2011/0015669 A1 * | 1/2011 | Corcosteugi ........ A61F 9/00736 |
| | | 606/207 |
| 2011/0077172 A1 | 3/2011 | Aizenberg et al. |
| 2011/0157278 A1 | 6/2011 | Gulvin et al. |
| 2012/0191120 A1 * | 7/2012 | Linsi ...................... A61F 9/007 |
| | | 606/174 |
| 2012/0302465 A1 | 11/2012 | Elmouelhi et al. |
| 2013/0059113 A1 | 3/2013 | Hatton et al. |
| 2013/0110222 A1 | 5/2013 | Slager |
| 2014/0120314 A1 | 5/2014 | Ho et al. |
| 2014/0182790 A1 | 7/2014 | Hwang et al. |
| 2014/0200679 A1 | 7/2014 | Bluecher et al. |

FOREIGN PATENT DOCUMENTS

| | | | |
|---|---|---|---|
| WO | 2010056933 A2 | 5/2010 | |
| WO | WO 2011094344 A1 * | 8/2011 | ............. B08B 17/06 |
| WO | WO 2012012441 A1 * | 1/2012 | ............. B08B 17/06 |
| WO | 2012167017 A2 | 12/2012 | |
| WO | 2014056782 A1 | 4/2014 | |

\* cited by examiner

MEDICAL DEVICES AND INSTRUMENTS WITH NON-COATED SUPERHYDROPHOBIC OR SUPEROLEOPHOBIC SURFACES

REFERENCE TO RELATED APPLICATION

This application claims priority from U.S. Provisional Patent Application Ser. No. 61/863,128, filed Aug. 7, 2013, the entire content of which is incorporated herein by reference.

FIELD OF THE INVENTION

This invention relates generally to devices that come in contact with liquids, fluids, oils, gels, and the like and, in particular, to methods and products of processes wherein at least a portion of such devices are rendered superhydrophobic and/or superoleophobic through microstructures and/or nanostructures that utilize the same base material(s) as the device itself.

BACKGROUND OF THE INVENTION

The term hydrophobic/philic is often used to describe the contact of a solid surface with any liquid. The term "oleophobic/philic" is used with regard to wetting by oil and organic liquids. The term "amphiphobic/philic" is used for surfaces that are both hydrophobic/philic and oleophobic/philic. Surfaces with high energy, formed by polar molecules, tend to be hydrophilic, whereas those with low energy and built of non-polar molecules tend to be hydrophobic.

The primary parameter that characterizes wetting is the static contact angle, which is defined as the angle that a liquid makes with a solid. The contact angle depends on several factors, such as surface energy, surface roughness, and its cleanliness. If a liquid wets the surface (referred to as wetting liquid or hydrophilic surface), the value of the static contact angle is $0 \leq \theta \leq 90$ degrees, whereas if the liquid does not wet the surface (referred to as a non-wetting liquid or hydrophobic surface), the value of the contact angle is 90 degrees $<\theta \leq 180$ degrees.

Surfaces with a contact angle of less than 10 degrees are called superhydrophilic, while surfaces with a contact angle between 150 degrees and 180 degrees are considered superhydrophobic. It is known that surfaces exhibiting microscopic roughness tend to be hydrophobic. With such surfaces, air is trapped between the liquid and the substrate, causing the value of the contact angle to be greater than 90 degrees. In nature, water droplets on the surface of a lotus leaf readily sit on the apex of organic nanostructures because air bubbles fill in the valleys of the structure under the droplet. Therefore, these leaves exhibit considerable superhydrophobicity. The static contact angle of a lotus leaf is about 164 degrees.

One of the ways to increase the hydrophilic properties of a surface is to increase surface roughness. Studies showed that for micro-, nano- and hierarchical structures, the introduction of roughness increased the hydrophobicity of the surfaces. One such hierarchical structure, composed of a microstructure with a superimposed nanostructure of hydrophobic waxes, led to superhydrophobicity with static contact angles of 173 degrees. (See, for example: Bhushan, B., Jung, Y. C., and Koch, K., "Micro-, Nano- and Hierarchical Structures for Superhydrophobicity, Self-Cleaning and Low Adhesion," *Phil. Trans. R. Soc. A* 367 (2009b) 1631-1672, the entire content of which is incorporated herein by reference.)

Micro-, nano- and hierarchical patterned structures have been fabricated using soft lithography, photolithography, and techniques which involve the replication of micropatterns, self assembly of hydrophobic alkanes and plant waxes, and a spray coating of carbon nanotubes. FIG. 1 is a schematic of a structure having an ideal hierarchical surface. Microasperities consist of the circular pillars with diameter D, height H, and pitch P. Nanoasperities consist of pyramidal nanoasperities of height h and diameter d with rounded tops. In essence, with such structures, the nanostructures prevent liquids from filling the gaps between the pillars.

There are numerous applications for hydrophobic surfaces, including self-cleaning, drag reduction, energy conservation and conversion. It has also been recognized that certain medical devices could benefit from hydrophobic surfaces. Published U.S. Application No. 2013/0110222, entitled MEDICAL DEVICES INCLUDING SUPERHYDROPHOBIC OR SUPEROLEOPHOBIC SURFACES, discusses the use of superhydrophobic/oleophopic surfaces for numerous medical applications, but it is clear from this reference that the disclosure is limited to superhydrophobic/oleophopic coatings as opposed to engineered microstructures or nanostructures that use the same base material as the device itself.

The preferred embodiments of the Published '222 Application prescribe the use of a slippery liquid-infused porous surface (SLIPS) comprising, for example, 1-butyl-3-methylimidazolium hexafluorophosphate. The Application states that "[s]tructured surfaces can also provide coatings, materials, or surfaces that are superhydrophobic, superoleophobic, or both. Suitable structure surfaces include those described in L. Mischchenko et al. ACS Nano 4 (12), 7699-7707 (2010), the disclosure of which is incorporated herein by reference. Suitable silicon nanostructures can be fabricated according to the Bosch process (citations from Published Application omitted). These nanostructures are then treated with a hydrophobic silane (e.g., tridecafluoro-1,1,2,2-tetrahydrooctyl)-trichlorosilane) by vapor exposure in a desiccator under vacuum overnight." ('222 Application; [0035]) "These structured surfaces can have geometrical features in the form of staggered bricks (e.g., subway brick pattern), posts, wide posts, blades, or honeycomb. Suitable geometrical features can be described by pitch, height, and wall/post thickness ratio . . . " ('222 Application; [0036]).

SUMMARY OF THE INVENTION

This invention relates generally to devices that come in contact with liquids, fluids, oils, gels, and the like and, in particular, to methods and products of processes wherein at least a portion of such devices are rendered superhydrophobic and/or superoleophobic through microstructures and/or nanostructures that utilize the same base material(s) as the device itself.

A medical device according to the invention includes a portion made from a base material having a surface adapted for contact with biological material, and wherein the surface is modified to become superhydrophobic, superoleophobic, or both, using only the base material, excluding non-material coatings. The surface may be modified using a subtractive process, an additive process, or a combination thereof. The product of the process may form part of an implantable device or a medical instrument, including a medical device or instrument adapted for use with an intraocular procedure.

In accordance with the invention, the surface adapted for contact with biological material is modified to include micrometer- or nanometer-sized structures or patterns made from the base material. For example, the surface may be modified to include micrometer- or nanometer-sized pillars, posts, pits or cavitations; hierarchical structures having asperities; or posts/pillars with caps having dimensions greater than the diameters of the posts or pillars.

DETAILED DESCRIPTION OF THE INVENTION

This invention improves upon existing designs by providing medical devices with hydrophobic/oleophobic surfaces using the same material(s) that such devices are constructed from; that is, without resorting to coatings. This is significant in that the substances used for such coatings may become detached during use and/or implantation, leading to contamination, infection, and other undesirable side-effects.

Figure 2:
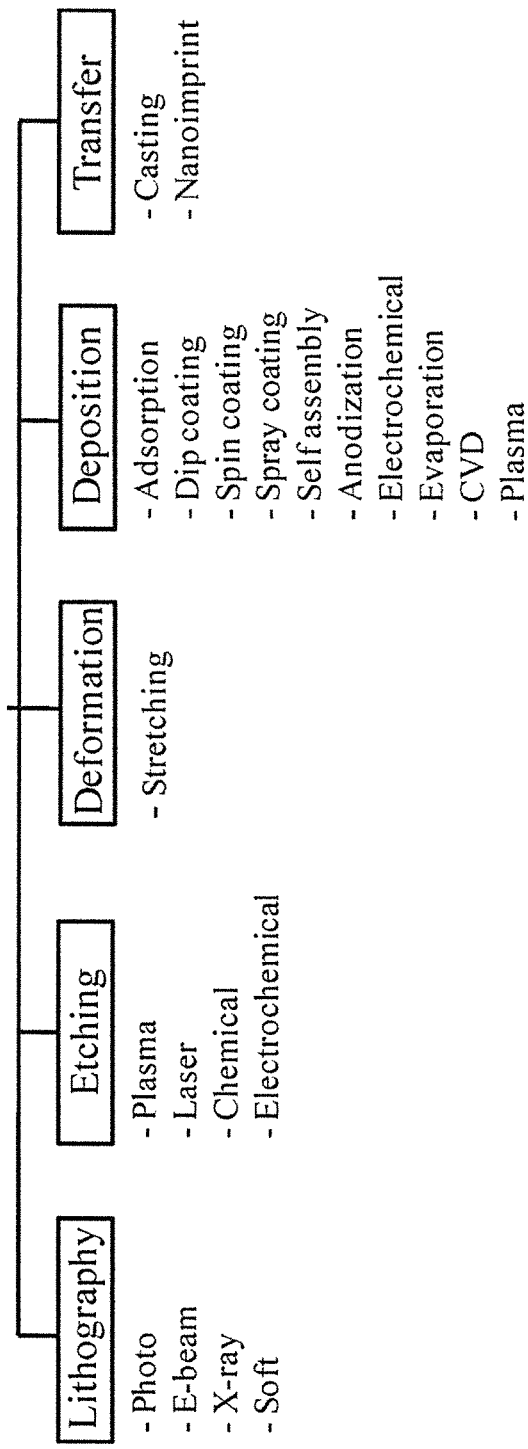
FIG. 2 is a diagram that shows potential fabrication techniques used to fabricate micron- and nano-scale structures.
Figure 3A:
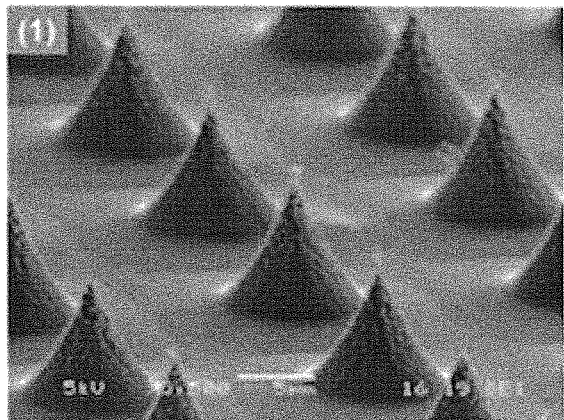
FIG. 3A shows an array of pointed conical shapes applicable to the invention.
Figure 3D:
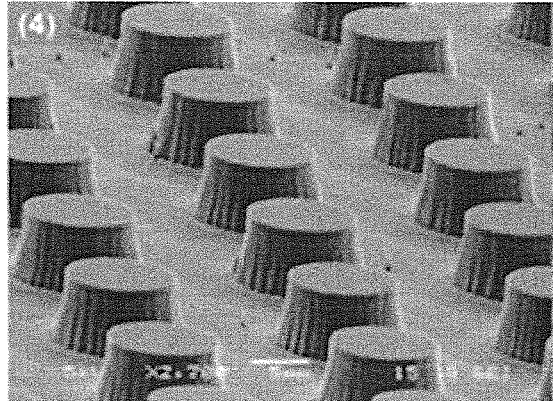
FIG. 3D shows an array of shorter, tapered pillars applicable to the invention.
Figure 3B:
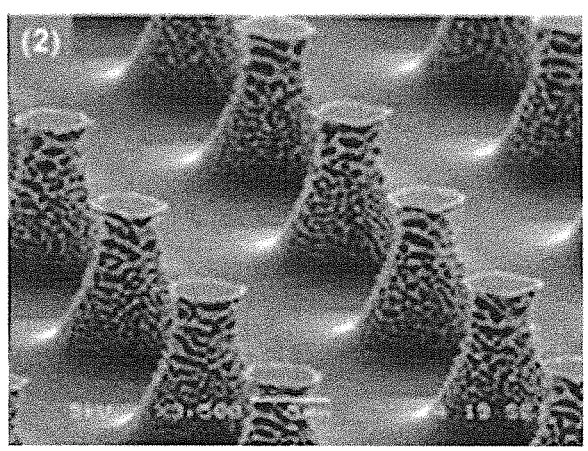
FIG. 3B shows an array of tapered pillars with caps applicable to the invention.
Figure 3E:
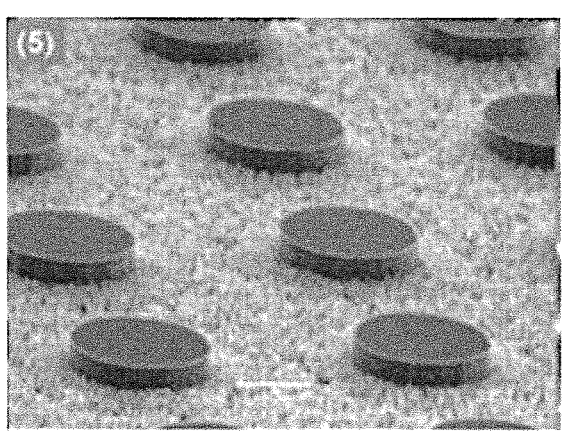
FIG. 3E shows an array of short, coin-like structures.
Figure 3C:
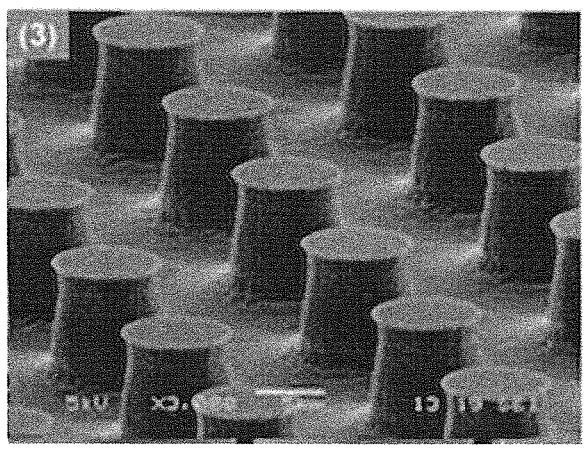
FIG. 3C shows an array of wider tapered pillars with caps applicable to the invention.
Figure 3F:
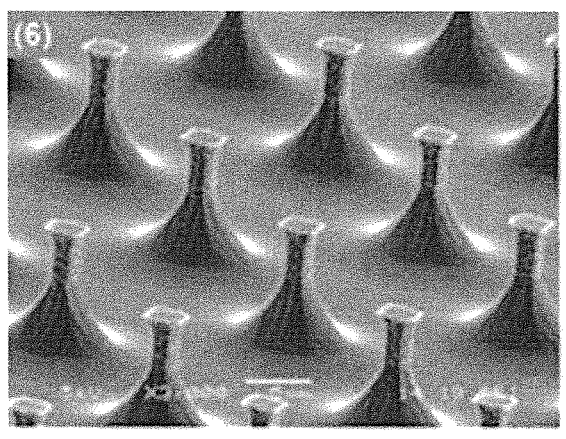
FIG. 3F shows an array of narrower, tapered pillars with caps applicable to the invention.

FIG. 2 is a diagram that shows potential fabrication techniques used to fabricate micron- and nano-scale structures. In the preferred embodiments, reduction processes (i.e., lithographic and/or etching) are preferred to additive steps such as deposition since the goal is to avoid material coatings. In the most preferred embodiments, e-beam lithographic and/or laser etching steps are used to create an array of pillars on the surface being modified. The invention does not preclude additive processes, however, so long as the same base material of the device is used to produce the additive microstructure. That is, if the base material is metal (i.e., stainless steel, chrome-cobalt, etc.), a metallic microstructure or nanostructure is additively formed to achieve a continuity in material type as opposed to dissimilar materials having a greater tendency to separate and flake off. Thus, processes requiring silicon (including the Bosch process), would not be recommended if a silicon coating is first required.

Figure 4A:
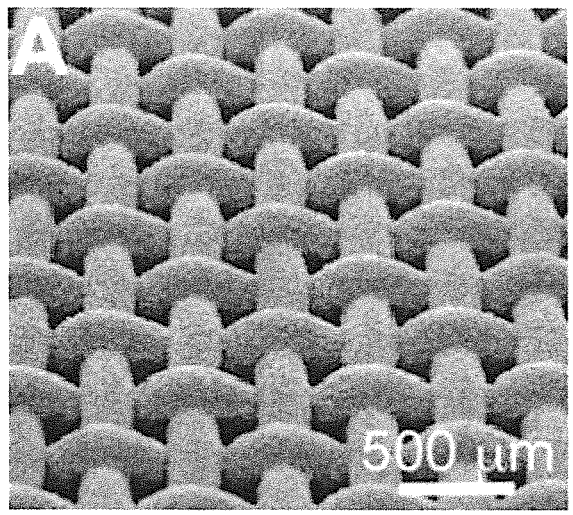
FIG. 4A illustrates a woven superomniphobic surface.
Figure 4B:
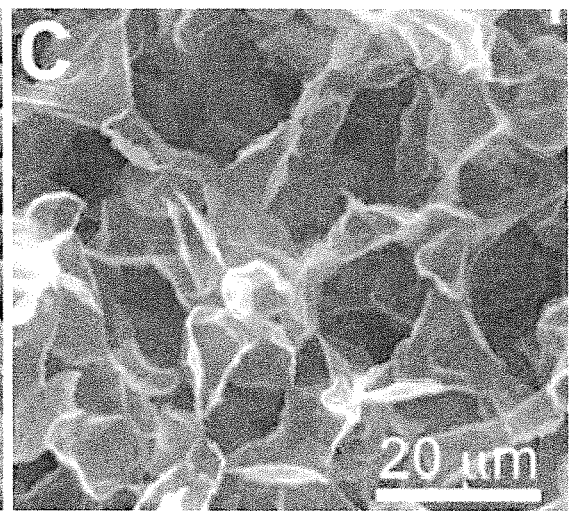
FIG. 4B illustrates a random superomniphobic surface.

Different micro-/nanostructures are applicable to the invention depending upon the hydrophobic and/or oleophobic properties to be achieved in view of a given application. FIGS. 3A-3F show arrays of shapes, certain of which may be more effective than other including pointed conical shapes and tapered pillars with and without caps. FIG. 4A illustrates a woven superomniphobic surface, and FIG. 4B illustrates a random superomniphobic surface.

Pillars formed in accordance with the invention may have straight sides or may have tapered sides. Pillars with any cross-sectional shape may be used, including circular or polygonal with 3, 4, 5, 6 or more sides. The pillars may have pointed or semi-pointed upper ends, as shown in FIGS. 3A-3F. Preferably, the pillars have a diameter (D) in the range of 10 microns or less, with a height (H) at least as tall as the pillars are wide. In more preferred embodiments, pillar height is 2-4 times the cross sectional height. Pillar spacing is preferably in the order of one to three times D.

Figure 5A:
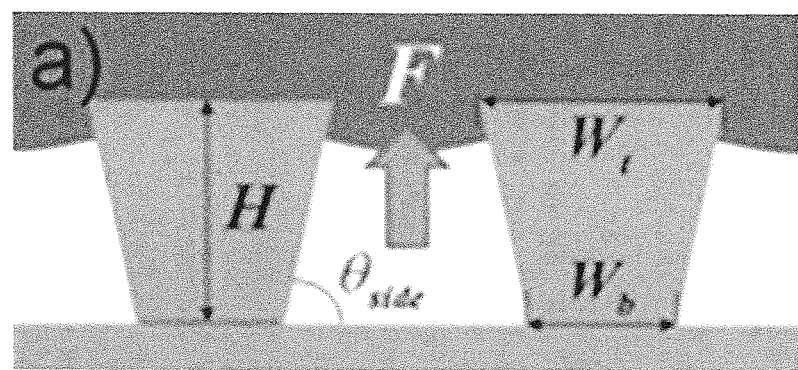
FIG. 5A shows a post or pillar having an inverse trapezoidal cross-section.
Figure 5B:
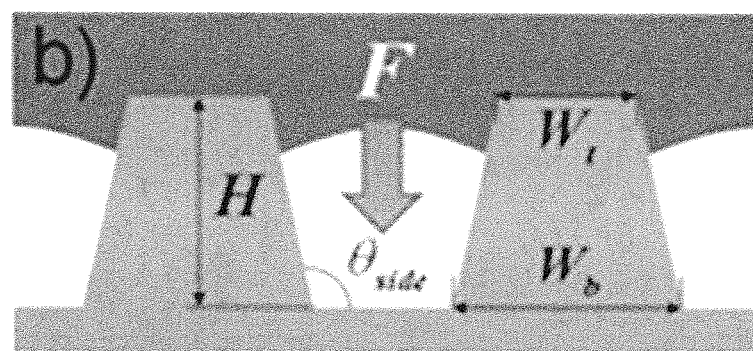
FIG. 5B shows a post or pillar having a non-inverted trapezoidal cross-section.
Figure 5C:
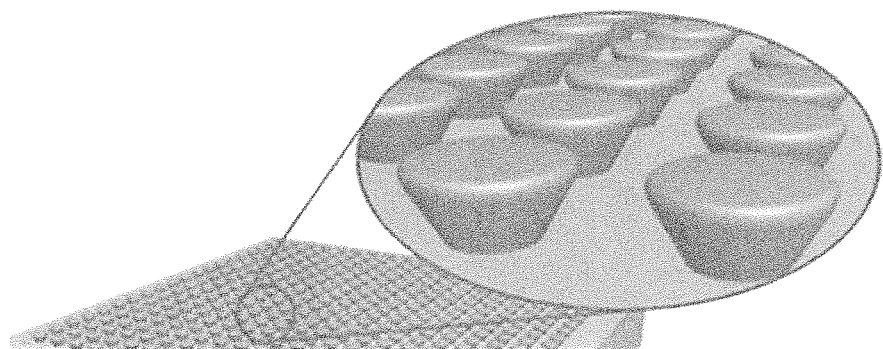
FIG. 5C depicts a preferred array of the structures of FIG. 5A.

The structures of FIGS. 5A-5C are considered to be particularly effective. FIG. 5A shows a post or pillar having an inverse trapezoidal cross-section; FIG. 5B shows a post or pillar having a non-inverted trapezoidal cross-section, and FIG. 5C depicts a preferred array of the structures of FIG. 5A.

Figure 1:
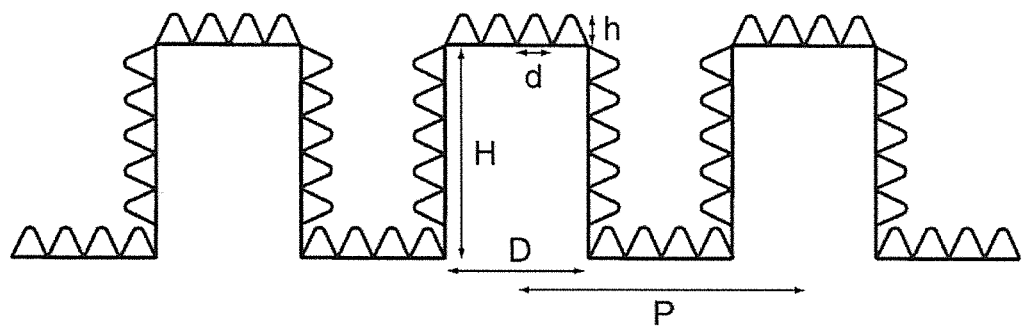
FIG. 1 is a schematic of a preferred structure having a hierarchical surface including asperities.

In certain preferred embodiments, the structure is hierarchical (FIG. 1) in the sense that one or more of the tops, sides, or spaces between the pillars includes asperities of height h in the range of 1 micron or less, depending upon the size of the pillars themselves. Preferably, the asperities are from 0.5 to .01 times the nominal thickness of the pillars, more preferably 0.1 times the nominal thickness. Such asperities may be produced via chemical etching following pillar formation.

Figure 6:
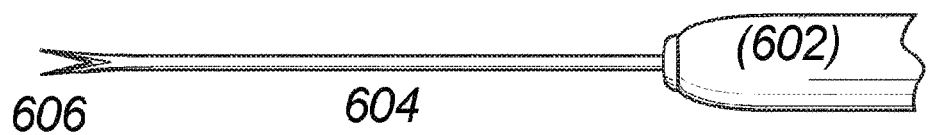
FIG. 6 is an illustration that depicts intraocular scissors.
Figure 7:
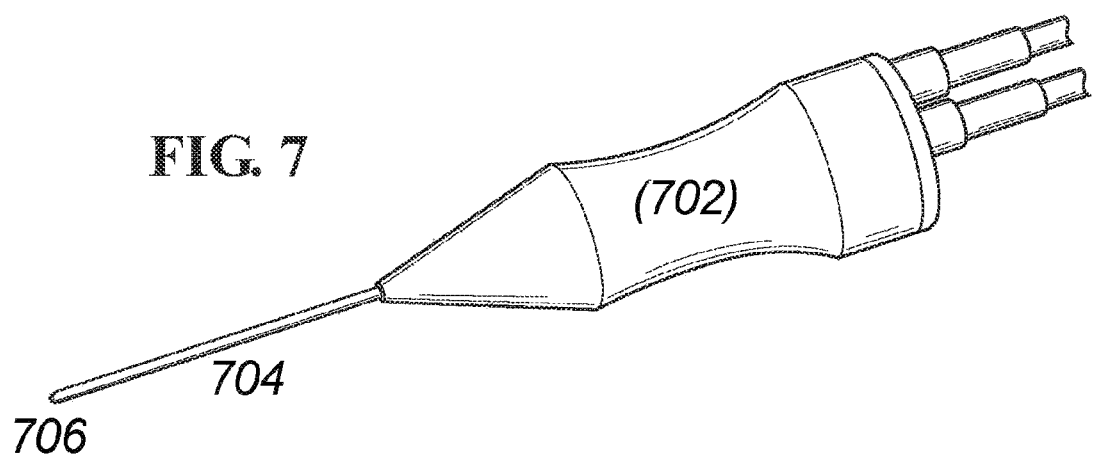
FIG. 7 is an illustration that shows a vitrectomy probe.
Figure 8:
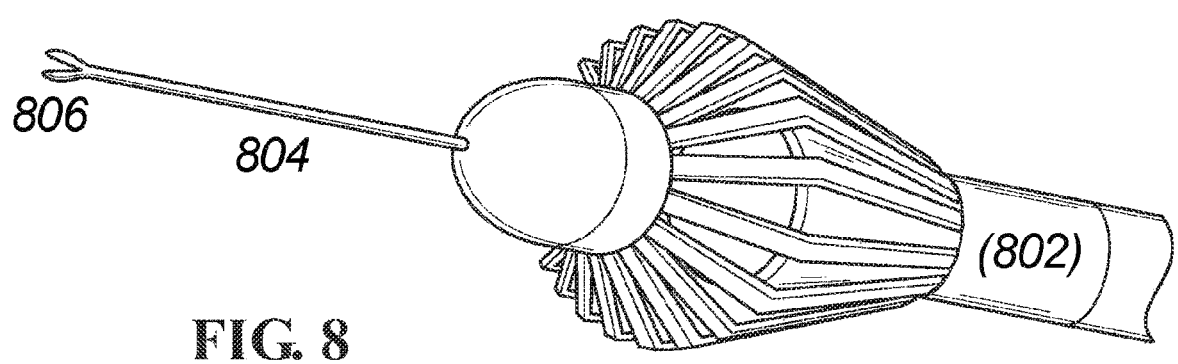
FIG. 8 is an illustration that depicts intraocular forceps.

The above, coating-free hydrophobic/oleophobic surface modifications may be used on any implantable on non-implantable medical device or instrument. Substrates of metal, ceramics—even plastics—may be modified through appropriate engineering modification to the energetic beams/etching modalities. The invention finds particular utility in providing surgical instruments having hydrophobic/oleophobic surfaces, and more particular those used in intraocular procedures. Such instruments include, without limitation, intraocular scissors (FIG. 6); vitrectomy probes (FIG. 7); and intraocular forceps (FIG. 8). Each instrument includes a respective proximal handle portion 602, 702, 802, and an elongated shaft 604, 704, 804 terminating in a distal tip 606, 706, 806 adapted for a particular intraocular procedure. In the event the instrument has one or more sharpened edges, such sharpening may be performed before or after the above surface modification, though sharpening following surface modification is preferred to produce the sharpest edge(s), while ensuring that any loose pillars are sloughed off prior to use:

The invention claimed is:

1. A medical instrument adapted for use with an intraocular procedure, comprising:
   a proximal portion configured for grasping by a user;
   a distal portion including an elongated shaft terminating in a distal tip adapted for use in conjunction with an intraocular procedure;
   wherein the distal portion is made from a base material having a surface adapted for contact with biological intraocular vitreous material; and wherein the surface of the distal portion of the instrument includes micrometer- or nanometer-sized structures or patterns made only from the base material, causing the distal portion of the instrument to become superhydrophobic, superoleophobic, or both, thereby causing the distal portion of the instrument to repel the vitreous material during the intraocular procedure.

2. The instrument of claim 1, wherein the micrometer- or nanometer-sized structures or patterns are pillars, posts, pits or cavitations using only the base material.

3. The instrument of claim 1, wherein the micrometer- or nanometer-sized structures include hierarchical structures having asperities.

4. The instrument of claim 1, wherein:
the micrometer- or nanometer-sized posts or pillars have diameters and upper caps with dimensions greater than the diameters of the posts or pillars.

5. The instrument of claim 1, wherein the micrometer- or nanometer-sized structures or patterns are formed using a subtractive process.

6. The instrument of claim 1, wherein the micrometer- or nanometer-sized structures or patterns are formed using an additive process.

7. The instrument of claim 1, wherein the micrometer- or nanometer-sized structures or patterns are formed using a combination of additive and subtractive processes.

8. The instrument of claim 1, wherein the elongated shaft terminates in intraocular scissors.

9. The instrument of claim 1, wherein the elongated shaft forms part of a vitrectomy probe.

10. The instrument of claim 1, wherein the elongated shaft terminates in intraocular forceps.

\* \* \* \* \*